US006783668B2

(12) United States Patent
Shirkhan

(10) Patent No.: US 6,783,668 B2
(45) Date of Patent: Aug. 31, 2004

(54) INTEGRATED PRESSURIZED LIQUID EXTRACTION AND PURIFICATION SYSTEM

(75) Inventor: Hamid Shirkhan, Newton, MA (US)

(73) Assignee: Fluid Management Systems, Inc., Waltham, MA (US)

( * ) Notice: Subject to any disclaimer, the term of this patent is extended or adjusted under 35 U.S.C. 154(b) by 0 days.

(21) Appl. No.: 10/682,684

(22) Filed: Oct. 9, 2003

(65) Prior Publication Data
US 2004/0069706 A1 Apr. 15, 2004

Related U.S. Application Data

(60) Provisional application No. 60/417,324, filed on Oct. 9, 2002.

(51) Int. Cl.[7] ............................. G01N 1/18; B01D 11/02
(52) U.S. Cl. .................... 210/137; 210/177; 210/198.2; 436/161; 422/69
(58) Field of Search ......................... 210/97, 137, 177, 210/198.2; 436/161; 422/69, 70

(56) References Cited

U.S. PATENT DOCUMENTS

2003/0096422 A1 * 5/2003 Ong et al. ..................... 436/91

OTHER PUBLICATIONS

Suomi, Johanna et al., Extraction of iridoid glycosides and their determination by micellar electrokinetic capillary chromatography, Journal of Chromatography A, vol. 868, Issue 1, Jan. 28, 2000, pp. 73–83.*
Dionex, Inc., ASE 200 Extraction System, www.dionex.com/app/tree.tafrasset_id=10988, Jul. 2003.
Environmental Protection Agency, Method 3545, Pressurized Fluid Extraction (PFE), Dec. 1996.
Fluid Management Systems, Inc., Sample Preparation: Power–Prep System, www.fms–inc.com/powerdes, 2003.

* cited by examiner

Primary Examiner—Terry K. Cecil
(74) Attorney, Agent, or Firm—Weingarten, Schurgin, Gagnebin & Lebovici LLP

(57) ABSTRACT

A system for pressurized liquid extraction and purification of solid samples includes a pressurized liquid extraction (PLE) module including a PLE cell, a heating element, a high-pressure source of an extraction solvent, a pressure regulator, and a cooling coil. The PLE module continuously performs high-pressure, high-temperature extraction on the solid sample to yield liquid sample. The liquid sample is concurrently provided to a purification module including one or more columns. The purification module yields a purified liquid sub-sample containing substantially all of a specific trace substance present in the solid sample. The sub-samples are transferred to a concentrator assembly through a collector inlet. The concentrated sub-sample can be used in subsequent analysis to determine the concentration of the trace substance in the original solid sample.

26 Claims, 3 Drawing Sheets

INTEGRATED PRESSURIZED LIQUID EXTRACTION AND PURIFICATION SYSTEM

CROSS REFERENCE TO RELATED APPLICATIONS

This application claims priority under 35 U.S.C. §119(e) of U.S. Provisional Patent Application No. 60/417,324 filed Oct. 9, 2002, the disclosure of which is hereby incorporated by reference herein.

STATEMENT REGARDING FEDERALLY SPONSORED RESEARCH OR DEVELOPMENT

Not Applicable

BACKGROUND OF THE INVENTION

The present invention is related to the field of agro-products, pharmaceutical production and sample analysis.

In the field of sample analysis, a large variety of studies are conducted in order to monitor for the presence of contaminants in food. In particular, toxins such as brominated and chlorinated pesticides, PCBs, and dioxins are extracted, purified and fractionated from pharmaceutical, environmental and biological samples. New and more stringent regulations regarding acceptable levels of these contaminants are continuously being adopted by the government or other regulatory agencies, driving the development of analytical systems that are more reliable and commercially practical. Important criteria in the development of such systems are the detection of more compounds, with lower detection limits, fast turn around and the ability to process a large number of samples efficiently. Currently, only a few laboratories can fulfill these emerging requirements.

Since chlorinated and brominated compounds are very toxic at sub-ppt (part per trillion) and ppqt (part per quadtrillion) levels, the purification of these compounds becomes a difficult task in sample analysis. It is necessary, for example, to protect the sample from interfering compounds during the extraction, purification and fractionation processes. Interfering compounds can be introduced from the air and surrounding environment.

For example, it is required to detect some PCBs in low ppt level in food samples. However, the amount of PCBs in the air and other surroundings of laboratories may exceed the detection limits of the sample, so that the laboratories are unable to perform accurate testing. As a result, lab testing facilities are forced to construct new clean room labs with controlled environments. Therefore, testing for these highly toxic compounds in food is becoming very difficult, and few labs are able to perform this testing.

In the field of agro-products, extracted, purified and separated end products are obtained from spices, herbs, aromatic plants, and medicinal plants and are used for various end use applications such as cosmetics, flavors, medicines, perfumes, etc.

In the field of pharmaceutical production, compounds of interest are extracted, purified and separated for use in producing drugs and supplements. These processes are similar to those used in sample analysis, although they are usually carried out on a much larger scale to provide a desired amount of product.

For several years, new extraction techniques have emerged that exhibit advantages such as lower solvent consumption, suitability for automation and higher throughput for processing solid and semi-solid samples such as food samples. The purification or "clean-up" step has also evolved from the early use of semi-automated stages to more recent use of entirely automated systems suitable for preparing a large number of samples. Nevertheless, there is a continuing need for fast, efficient systems for performing high-quality sample analysis and pharmaceutical production.

BRIEF SUMMARY OF THE INVENTION

In accordance with the present invention, a system is disclosed for pressurized liquid extraction and purification of solid biological materials (also referred to herein as "samples) containing trace substances that may be the subject of subsequent analysis or that may be used as an ingredient in a pharmaceutical product. The system may be used, for example, in the extraction, purification and fractionation of trace substances such as chlorinated pesticides, PCBs, pesticides and brominated compounds.

Extraction, purification and fractionation are performed in a closed loop system, which reduces the exposure of the sample to the air and surrounding environment. In the case of sample analysis, hundreds of toxins such as dioxins, PCBs and pesticides can be detected at low levels in a single run at generally high speed. High-quality food sample analysis can therefore be performed, which is required to protect the population from contaminants from a variety of sources, such as agricultural and environmental sources or from terrorist activities.

The disclosed system employs an integrated extraction, purification and fractionation system for detection of toxins at levels as low as ppqt in a closed loop system. The system includes a pressurized liquid extraction (PLE) module that includes a solvent selection valve, a PLE cell, a heating element thermally coupled to the PLE cell with over temperature shutoff, a high-pressure pump coupled to an input port of the PLE cell, and a pressure regulator coupled between an output port of the PLE cell and an input port of a cooling coil. The output port of the cooling coil is connected to the output port of the PLE module. The cooling coil conditions the temperature of the extract and transfers the cooled extract to the input of a purification module. The PLE module continuously performs high-pressure, high-temperature extraction on the solid sample to yield liquid sample, and concurrently provides the liquid sample to the output port of the PLE module.

The system further includes a purification module having a sample input port coupled to the output port of the PLE module. The purification module operates concurrently with the extraction of the liquid sample by the PLE module to separate a purified liquid sub-sample from the liquid sample and to fractionate chlorinated dioxins, PCBs, pesticides, and brominated compounds. The fractionated sub-samples contains all or nearly all of the trace substance present in the solid sample. The purified fractions are concentrated in a concentration assembly and can be utilized in subsequent analysis to determine the concentration of hundreds of targeted trace substances in the sample.

The system provides rapid detection of hundreds of the most toxic compounds in food. In addition, it minimizes the need for giant clean room labs which otherwise might be necessary to perform testing and detection of those toxins. The system also simplifies sample handling inside the laboratory and can reduce sample preparation time to less than two hours. Finally, the system can accommodate many types of solid matrices, including those that must be processed in large quantities.

Other aspects, features, and advantages of the present invention will be apparent from the Detailed Description that follows.

BRIEF DESCRIPTION OF THE SEVERAL VIEWS OF THE DRAWINGS

The invention will be more fully understood by reference to the following Detailed Description of the invention in conjunction with the Drawing, of which.

DETAILED DESCRIPTION OF THE INVENTION

Figure 1:
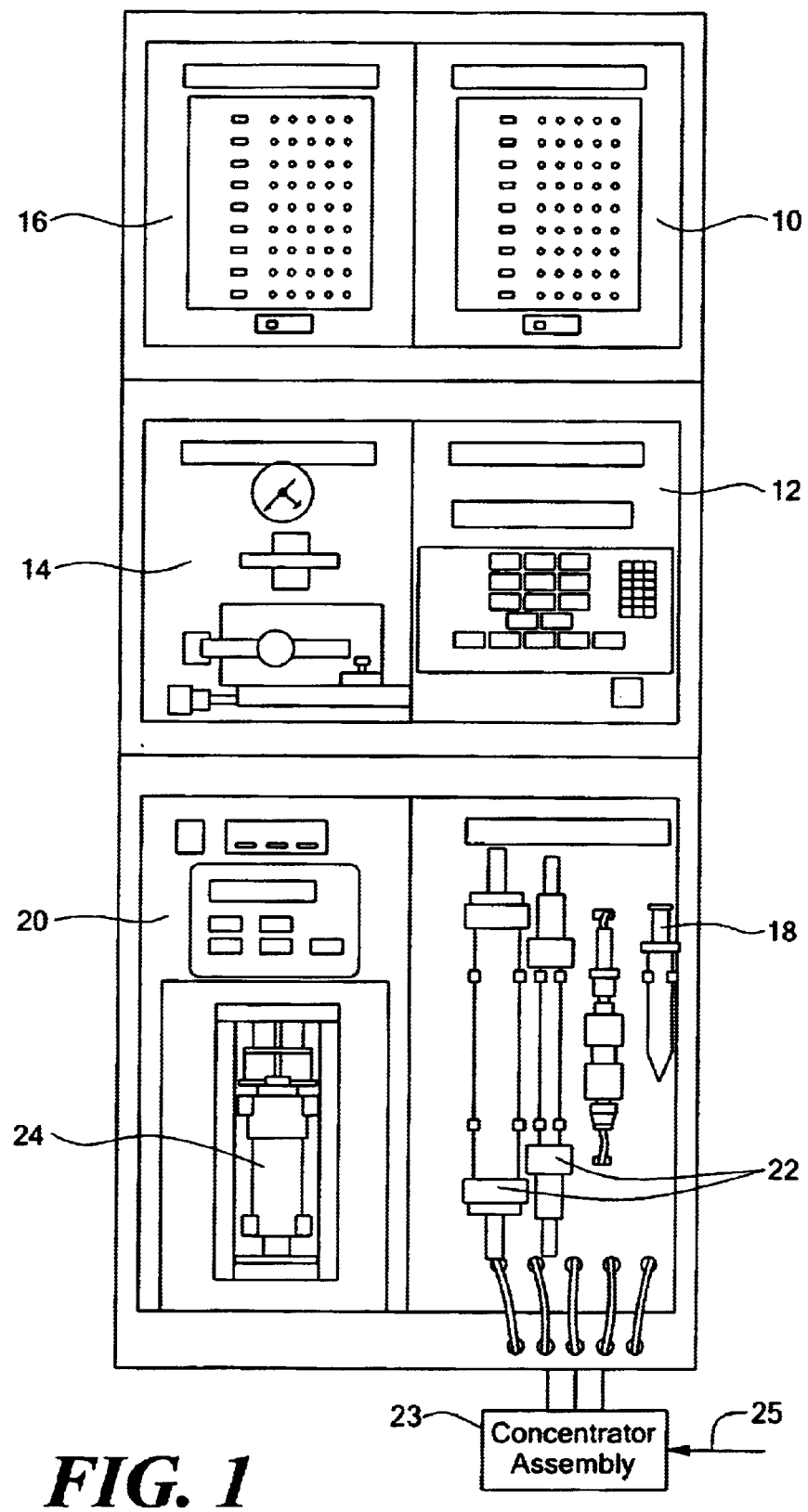
FIG. 1 is an illustration of a front view of a pressurized liquid extraction (PLE) and purification system in accordance with the present invention.

FIG. 1 shows a front view of an integrated pressurized liquid extraction (PLE) and purification system that can be used to test a variety of solid and semi-solid samples for the presence of any of a number of trace substances. The system includes a power supply module 10, a control module 12, a pump and pressure control module 14, a valve drive module 16, sample processing (purification) module 18, and PLE module 20. As shown, the purification module 18 contains a number of columns 22 used in separation/purification processes as described below. Outputs of the purification module 18 are coupled to concentrator assembly 23, which also receives nitrogen from an inlet 25. The PLE module 18 includes a stainless steel PLE cell 24 in which the pressurized liquid extraction occurs. A personal computer (not shown in FIG. 1) communicates with the control module 12 and provides editing, storage of extraction and purification, and separation program as well as real time monitoring and recording of pressure, temperature and status of all control valves.

As mentioned, the system can be used in pharmaceutical and food production applications, which are generally of larger scale than laboratory analysis application. In such large scale environments, the system is used with a large scale PLE extraction cell, heating elements, and large scale purification columns. These items can be placed on a separate rack and connected to the same column ports to which the corresponding smaller-scale columns are connected in an analysis environment.

The power supply module 10 supplies electrical power to the system. The control module 12 controls the operation of the other system modules, including the settings of various valves as described below. The control module 12 includes a display and keypad for local operator control, and also includes an interface to a separate controller such as a personal computer running a control program (not shown).

The pump and pressure control module 14 includes a piston pump used for low-pressure delivery of solvents and sample. Additionally, it includes components for pressure monitoring, overpressure control and alarms. The valve drive module 16 provides drive power to the various valves in the system (described below).

Figure 2:
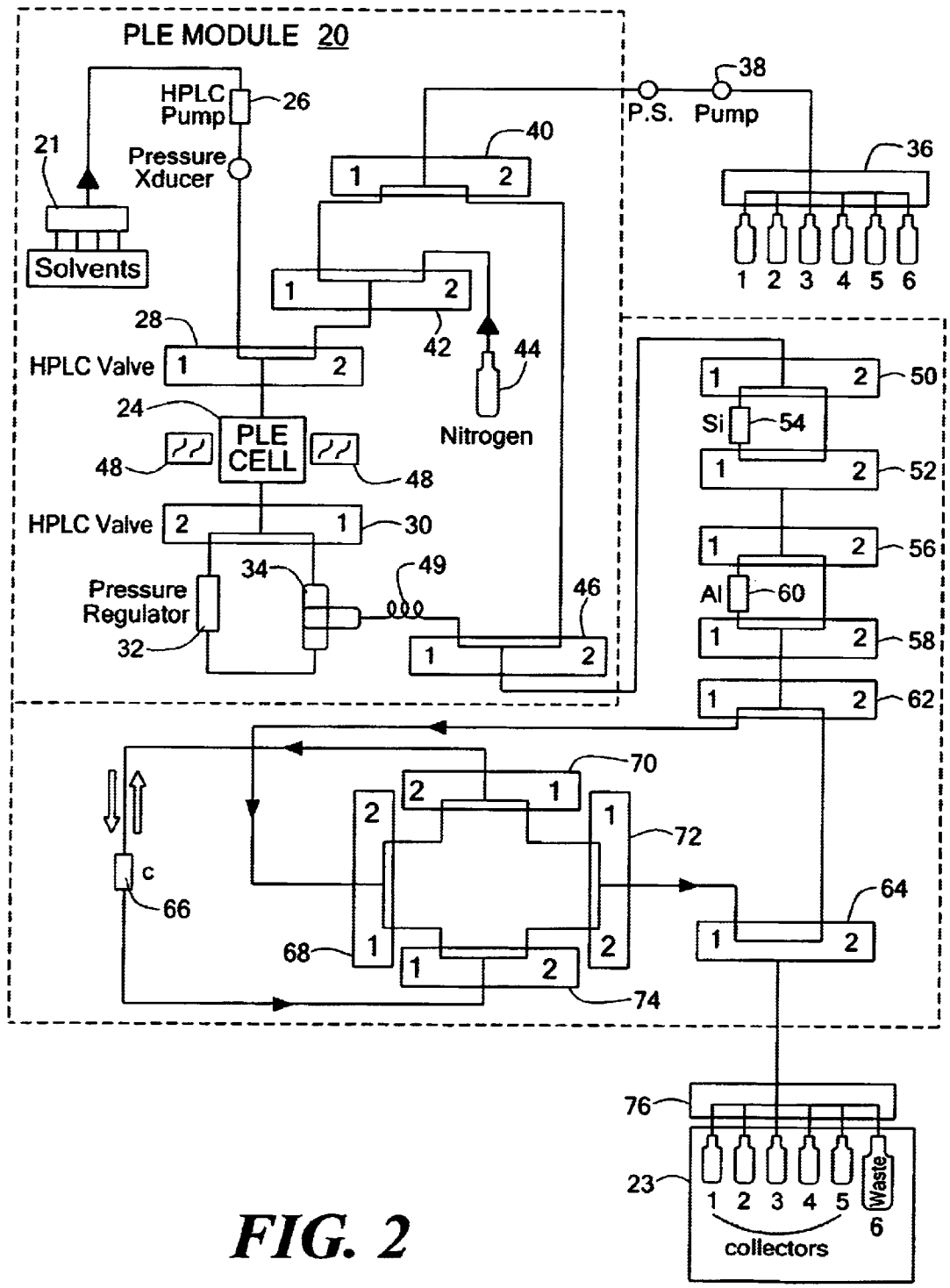
FIG. 2 is a schematic diagram of the PLE and purification system of FIG. 1.

FIG. 2 shows the internal configuration of the system of FIG. 1. Within the PLE module 20, a solvent select valve 21 is coupled to a high-performance liquid chromatography (HPLC) pump 26, which is coupled through an HPLC valve 28 to the input port of the PLE cell 24. The solvent select valve 24 provides the option to select step or binary gradient of any combination of various solvents. The output port of the PLE cell 24 is coupled via a second HPLC valve 30 to a pressure regulator 32 and a T fitting 34. As shown, the PLE module 20 also receives input from a source 36 of solvents via another pump 38. This input is provided through valves 40 and 42 to a second input of the HPLC valve 28. The valve 42 also receives the output of a nitrogen source 44. Another valve 46 selects between the output of PLE cell 24 (via T fitting 34) and sample/solvent from valve 40. Additionally, the PLE cell 24 is surrounded by a heating element 48 that is responsible for maintaining a high temperature within the PLE cell 24 during extraction. Typical extraction temperatures are in the range of 120 to 150 degrees Celsius.

The output of the T-fitting 34 is connected to a cooling coil 49, which in turn is connected to a valve 46. The output of the valve 46, which serves as the output port of the PLE module 20, is provided to one of a pair of valves 50, 52 associated with a silica column 54 within the purification module 18. The valves 50 and 52 can be used to selectively bypass the silica column 54. The output of valve 52 is provided to one of a second set of valves 56, 58 associated with an alumina column 60. The output of valve 58 is provided to one of a third set of valves 62, 64 associated with a carbon column 66. Also associated with the carbon column 66 are a set of four valves 68, 70, 72 and 74 that provide for bidirectional flow of fluid through the carbon column 66. The output of the valve 64 is provided to a set of collectors 76 in the concentrator assembly 23 for the separated components as well as waste fluid.

The various pumps and valves shown in FIG. 2 are controlled in accordance with one or more separation programs or "protocols" that each involve a sequence of steps. At each step, the valves are set in a way that provides for fluid flow along some desired path in the system to accomplish a corresponding part of the protocol. These steps include, for example, running rinse fluids through valves and/or columns, running extraction solvents into columns, running sample into the columns, and running purified samples into the collectors. The control of the components of the purification module 18 to create purified extract which contains toxins such as dioxins, PCBs etc. using solvents is generally within the skill of the art, and therefore is not further elaborated.

The plumbing of the system as illustrated in FIG. 2 allows for control of the flow rate at the downstream side of the PLE cell 24, resulting in the production of a constant solvent flow independent of applied pressure and temperature. The following characteristics result from this feature of the system: 1) an efficient mass transfer rate, 2) a steady supply of fresh solvent to the PLE cell 24, 3) constant feeding of the silica column 54, and 4) reduced clogging of the PLE cell 24 that can arise due to static residence time of the solvent.

Figure 3:
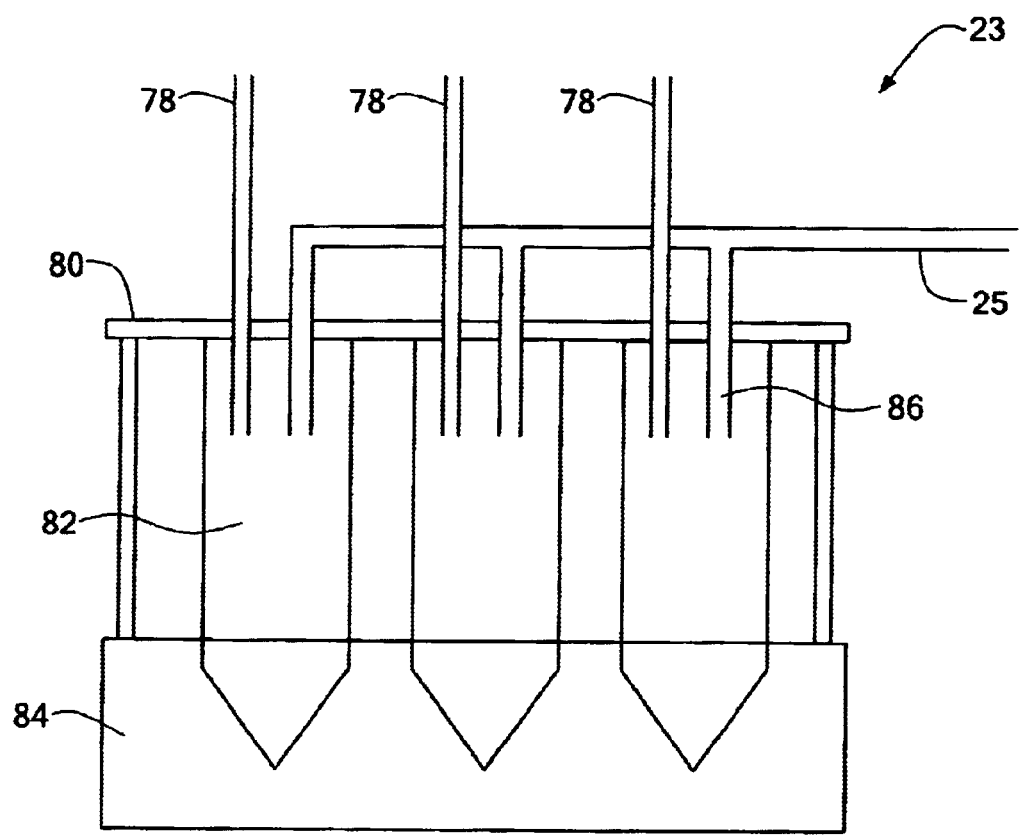
FIG. 3 is a diagram of a concentrator assembly in the system of FIGS. 1 and 2.

FIG. 3 shows the concentrator assembly 23. It includes fraction inlets 78 from the purification module 18 (FIGS. 1 and 2), a collection cover 80, collector vials 82 and a heating pad 84. The nitrogen inlet 25 is coupled to stainless steel needle inlets 86 extending into the vials 82.

Various food-stuff samples representative of samples processed in a monitoring laboratory have been investigated, including items such as Camembert cheese, Atlantic salmon, pork meat, bovine fat, egg yolks, and certain animal feedstuffs. Fat content ranged between 10 and 90% on a fresh weight basis. After homogenization, the samples were lyophilised to remove water, and the dried matrices were then manually ground to produce a fine powder ready for PLE.

The amount of dried sample processed through the on-line extraction and clean-up ranged between 5 and 35 g (0.5 to 8 g of fat).

Extractions were performed using hexane as a solvent. Temperatures ranged between 120 and 150° C., and the pressure was between 2000 and 4000 PSI, depending on the matrix. Nitrogen gas (20 PSI, 1 min.) was applied at the end of the extraction to achieve release of solvent remaining in the PLE cell 24 through the silica column 54. A classical clean-up program was used to complete the sample preparation and perform the fractionation process, yielding purified extracts either in hexane:dichloromethane (PCBs) or in toluene (PCDD/Fs and cPCBs). Recovery rates were comparable to those attained using prior art methods. It is believed that the continuous aspect of the extraction and the selection of quite high pressure (3500 PSI) plays an important role in extraction yield and in avoiding extraction of undesirable components when toluene is used as a solvent.

It will be apparent to those skilled in the art that modifications to and variations of the disclosed methods and apparatus are possible without departing from the inventive concepts disclosed herein, and therefore the invention should not be viewed as limited except to the full scope and spirit of the appended claims.

What is claimed is:

1. A system for pressurized liquid extraction and purification of a solid sample containing at least one trace substance, comprising:
   a pressurized liquid extraction (PLE) module including a PLE cell, a heating element thermally coupled to the PLE cell, a high-pressure source of an extraction solvent coupled to an input port of the PLE cell, a pressure regulator coupled to an output port of the PLE cell, and a cooling coil coupled between an output of the pressure regulator and an output port of the PLE module, the PLE module being operative to (1) continuously perform high-pressure, high-temperature extraction on the solid sample to yield hot liquid sample, and (2) concurrently feed the hot liquid sample to the cooling coil to yield cooled liquid sample while preventing attraction of interferences and contaminants from the air, the cooled liquid sample being provided to the output port of the PLE module; and
   a purification module having a sample input port coupled to the output port of the PLE module, the purification module being operative concurrently with the extraction of the liquid sample by the PLE module to separate a liquid sub-sample from the liquid sample, the liquid sub-sample containing substantially all of the trace substance present in the solid sample.

2. A system according to claim 1, wherein the purification module includes a column operative to collect the trace substance and to release the trace substance into a solvent to create the liquid sub-sample.

3. A system according to claim 2, wherein the column is a silica column.

4. A system according to claim 2, wherein the column is a carbon column.

5. A system according to claim 2, wherein the column is an alumina column.

6. A system according to claim 2, wherein the column is a first HPLC column of a first material, and wherein the purification module further includes one or more additional columns of respective materials different from the first material.

7. A system according to claim 6, wherein the first column is of silica and the additional columns include a column of aluminum and a column of carbon.

8. A system according to claim 7, further comprising a set of valves operative to establish bidirectional flow of fluid through the carbon column.

9. A system according to claim 1, wherein the liquid sub-sample is a first liquid sub-sample and the trace substance is a first trace substance, and wherein the purification module is further operative to separate out a second liquid sub-sample from the liquid sample, the second liquid sub-sample containing substantially all of a second trace substance present in the solid sample.

10. A system according to claim 1, wherein the extraction is performed in the temperature range of 100 to 150 degrees Celsius.

11. A system according to claim 1, wherein the extraction is performed in the pressure range of 2000 to 4000 PSI.

12. A system according to claim 1, further comprising a solvent selection valve operative to generate the extraction solvent from a combination of different organic solvents.

13. A system according to claim 1, wherein the extraction solvent comprises toluene.

14. A system according to claim 1, wherein the extraction solvent comprises partially hexane and partially a combination of other organic solvents.

15. A system according to claim 14, wherein the combination of other organic solvents includes toluene and dichloromethane.

16. A system according to claim 1, wherein the solid sample comprises a food-stuff.

17. A system according to claim 14, wherein the food-stuff comprises fatty animal tissue.

18. A system according to claim 1, wherein the solid sample comprises a solid pharmaceutical, environmental or biological sample.

19. A system according to claim 1, wherein the solid sample comprises a semi-solid pharmaceutical, environmental or biological sample.

20. A system according to claim 1, wherein the solid sample comprises a food-stuff and the trace substance comprises a contaminant thereof.

21. A system according to claim 20, wherein the contaminant comprises a dioxin.

22. A system according to claim 20, wherein the contaminant comprises a polychlorinated biphenyl (PCB).

23. A system according to claim 20, wherein the contaminant comprises a polybrominated diethyl ether (PBD).

24. A system according to claim 20, wherein the contaminant comprises a pesticide.

25. A system according to claim 1, further comprising a set of solvent sources, and wherein the PLE module further includes an input valve and an output valve, the input valve selectively directing solvent from the set of solvent sources to either the PLE cell or to the output valve, the output valve selectively directing either the liquid sample or a solvent from the set of solvent sources to the input port of the purification module.

26. A pressurized liquid extraction (PLE) module, comprising:
   a PLE cell;
   a heating element thermally coupled to the PLE cell;
   a high-pressure source of an extraction solvent coupled to an input port of the PLE cell;
   a pressure regulator coupled to an output port of the PLE cell; and
   a cooling coil having an input port coupled to an output port of the pressure regulator, the cooling coil being operative to provide clean and interference free conditioning of liquid extract while preventing attraction of interferences and contaminants from the air, and to provide cooled liquid sample to an output port of the PLE module for further processing.

* * * * *